(12) United States Patent
Inwald et al.

(10) Patent No.: US 12,205,705 B2
(45) Date of Patent: Jan. 21, 2025

(54) SMART NUTRITION DOSING

(71) Applicant: OptimDosing LLC, Farmington Hills, MI (US)

(72) Inventors: David Inwald, Berkley, MI (US); Kenneth I. Kohn, West Bloomfield, MI (US)

(73) Assignee: OptimDosing LLC, Farmington Hills, MI (US)

( * ) Notice: Subject to any disclaimer, the term of this patent is extended or adjusted under 35 U.S.C. 154(b) by 220 days.

(21) Appl. No.: 17/380,059

(22) Filed: Jul. 20, 2021

(65) Prior Publication Data

US 2022/0028527 A1    Jan. 27, 2022

Related U.S. Application Data

(60) Provisional application No. 63/055,288, filed on Jul. 22, 2020.

(51) Int. Cl.
*G16H 20/60* (2018.01)
*G16H 10/60* (2018.01)
*G16H 20/13* (2018.01)
*G16H 20/17* (2018.01)
*G16H 50/70* (2018.01)

(52) U.S. Cl.
CPC ............. *G16H 20/60* (2018.01); *G16H 10/60* (2018.01); *G16H 20/13* (2018.01); *G16H 20/17* (2018.01); *G16H 50/70* (2018.01)

(58) Field of Classification Search
CPC ........ G16H 20/60; G16H 10/60; G16H 20/13; G16H 20/17; G16H 50/70; G16H 15/00; G16H 50/20
See application file for complete search history.

(56) References Cited

U.S. PATENT DOCUMENTS

| | | | | |
|---|---|---|---|---|
| 7,295,889 B2* | 11/2007 | Lahteenmaki | ......... | G16H 20/60 700/239 |
| 8,060,354 B2* | 11/2011 | Dodds | ..................... | G16B 50/00 703/11 |
| 2004/0265874 A1* | 12/2004 | Binder | .............. | G06F 18/24147 435/6.16 |
| 2005/0176057 A1* | 8/2005 | Bremer | .............. | G01N 33/5082 435/6.16 |
| 2014/0094745 A1* | 4/2014 | Bashan | .................. | G16H 20/10 702/19 |

(Continued)

*Primary Examiner* — Eliza A Lam
(74) *Attorney, Agent, or Firm* — Kohn & Associates PLLC; Kenneth I. Kohn; Laura S. Dellal (57) ABSTRACT

A method of dosing food and nutrients for an individual patient, by collecting data from the individual patient including food and nutrients to be taken by the patient, analyzing the data in view of dosing criteria established based on outside data, and determining a dose for each food and nutrient taken by the individual patient. A logic engine for dosing food and nutrients, including an algorithm stored on non-transitory computer readable media for collecting outside data to establish criteria for dosing food and nutrients to an individual patient and patient data and storing outside data and patient data in a database, analyzing the individual patient data in view of criteria established from the outside data, and determining a dose for each food and nutrient to be taken.

14 Claims, 4 Drawing Sheets

(56) References Cited

U.S. PATENT DOCUMENTS

| | | | | |
|---|---|---|---|---|
| 2014/0255882 A1* | 9/2014 | Hadad | ............... | G09B 19/0092 |
| | | | | 434/127 |
| 2014/0351197 A1* | 11/2014 | Mould | .................. | G16H 20/10 |
| | | | | 706/52 |
| 2019/0267128 A1* | 8/2019 | Decombel | .............. | G16H 20/60 |
| 2020/0066181 A1* | 2/2020 | Hadjigeorgiou | ....... | G16H 20/60 |

\* cited by examiner

SMART NUTRITION DOSING

BACKGROUND OF THE INVENTION

1. Technical Field

The present invention relates to methods of determining dosing of food and nutrition. More specifically, the present invention relates to methods, software, and algorithms for determining nutrient doses for an individual patient or a patient population based on compilation and analysis of clinical study data.

2. Background Art

World Health Organization (WHO) reported that approximately 826 million people in the world are undernourished—792 million people in the developing world and 34 million in the developed world.

Malnutrition is a broad term that can be used to describe any imbalance in nutrition; from over-nutrition often seen in the developed world, to under-nutrition seen in many developing countries, but also in hospitals and residential care facilities in developed nations. It is not necessarily caused by a lack of food, and it is not unique to poor populations, but is a common problem in patients with chronic or severe diseases.

Even in first world nations, there are malnourished people. In the United States, for example, disease associated malnutrition (DAM) affects up to 15% of ambulatory outpatients, 25%-60% of patients receiving long-term care, and 35%-65% of hospitalized patients. DAM is costly to our healthcare system and proper nutrition could lessen this cost, especially if malnutrition caused by chronic diseases is better addressed through early engagement. One potential area for dramatic cost reductions is hospital readmissions.

157 Million Americans (nearly 50% of the population) will experience at least one chronic illness in their lifetime. Persons with multiple chronic conditions may have rapid declines and a greater likelihood of long-term disability. Studies have repeatedly shown that clinical malnutrition has serious implications for recovery from disease, trauma and surgery and is generally associated with increased morbidity and mortality both in acute and chronic diseases. Contributing factors to death include a lack of sufficient nutrient testing, a lack of communication between patients and health care providers, patients' lack of understanding the warning signs of malnutrition, and confusion on the patients' part regarding strong dietary choices and individual nutrition imbalances. Maintaining healthy nutrition is also a struggle during treatment due to severe side effects that interfere with the ability to taste, swallow, cook, and shop. Certain diseases can also cause nutrients and calories to not be able to be efficiently absorbed, such as with cancer of the pancreas, stomach, or digestive tract diseases. This can cause further wasting of the person, which can accelerate disease progress or cause additional side effects. Such problems are particularly difficult for persons undergoing chemotherapy.

About 85% of Americans do not consume the US Food and Drug Administration's recommended daily intakes of the most important vitamins and minerals necessary for proper physical and mental development. When people do not get enough of the nutrients they need for good health, they run the risk of becoming malnourished.

Vitamin deficiencies are a form of malnutrition, and one vitamin deficiency in particular has become a health concern in the United States. For example: more than 75 percent of Americans are deficient in vitamin D, according to a 2009 study published in the "Archives of Internal Medicine. Eating disorders, some medical conditions, and obesity can also lead to malnourishment. Celiac disease, chronic liver disease, Cohn's disease, and some cancers can affect the body's ability to absorb sugars, fats, proteins and vitamins. Certain medications can also limit the body's ability to absorb nutrients, as can surgical procedures designed to treat obesity. Further, those who are anorexic, bulimic or obese run the risk of malnutrition because they do not get enough of the right nutrition, or that nutrition never reaches the stomach.

There are several applications and devices that are using artificial intelligence to improve nutrition. Nutrino is a leading provider of nutrition-related data services, analytics, and technologies. Nutrino uses artificial intelligence to predict and tailor foods and recipes to users and includes hydration and mood tracking in an application to make recommendations to users. A FOODPRINT™ is used in making recommendations that uses how a person's body reacts to different foods. SmartPlate uses a plate that can visually determine food placed thereon, weigh portions, and report caloric and nutritional data to an app. Suggestic is an app that helps users reverse Type 2 Diabetes by using machine learning technology that creates an individualized nutrition and lifestyle program based on factors such as DNA, blood, saliva and gut microbiome, diet and activity logs.

Machine learning techniques have been applied to nutritional intake information for the purpose of weight loss (US20140221785A1). Such systems gather information from the user (user-inputted data and/or integrations with fitness trackers, smart scales, etc.) and prepare a report/dashboard highlighting changes in the tracked components over time. In the scope of weight loss, generally the information tracked includes overall calories consumed, the nutritional breakdown of food consumed, and fitness activities. The only application of artificial intelligence and machine learning is in displaying the trends of tracked data over time. Such systems lack a predictive element that incorporates identified trends as conditions for a more complex model. Further, since these widely available systems are limited to calories and nutritional components, they do not consider other variables related to well-being including specific adverse events, psychological stress, symptoms of chronic conditions, etc.

Therefore, there remains a need for an effective method of managing nutrition and suggesting appropriate doses based on the patient's disease state and nutrition state.

SUMMARY OF THE INVENTION

The present invention provides for a method of dosing food and nutrients for an individual patient, by collecting data from the individual patient including food and nutrients to be taken, analyzing the individual patient data in view of dosing criteria established based on outside data, and determining a dose for each food and nutrient taken by the individual patient.

The present invention further provides for a logic engine for dosing food and nutrients, including an algorithm stored on non-transitory computer readable media for collecting outside data to establish criteria for dosing food and nutrients to an individual patient and storing outside data and patient data in a database, analyzing the individual patient data in view of criteria established from the outside data, and determining a dose for each food and nutrient to be taken.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
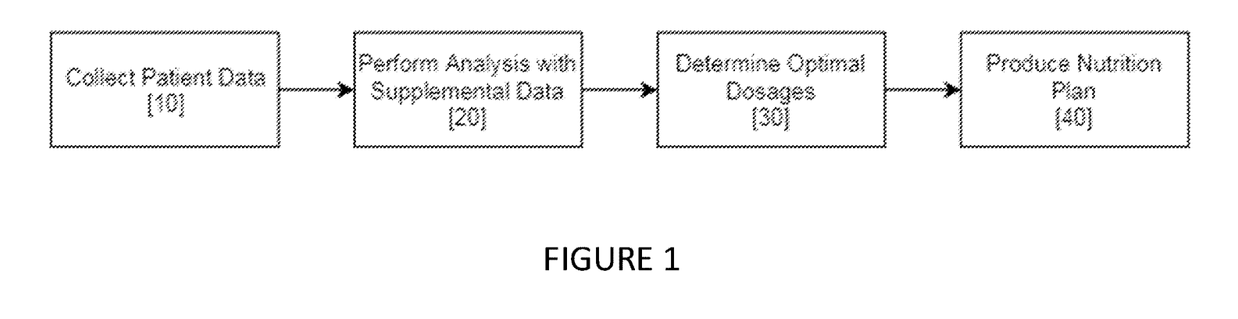
FIG. 1 is a schematic of the method of the present invention.

The present invention generally provides for methods of dosing food and nutrients to ensure that patients receive a safe and effective dose of food/nutrients and provides patients with a nutritional plan. Most generally, as shown in FIG. 1, the method includes collecting patient data 10 with treatment plan details including information from Electronic Medical Records, past/current nutritional intake habits, laboratory results such as Complete Blood Count, food/nutrients to be taken, analyzing the data in view of outside supplementary data 20, and determining an optimized dose for each food/nutrient 30. The results from running the model 30 are used to prepare a comprehensive nutrition plan 40. The present invention is particularly useful in managing nutrition of patients with cancer or other disease states. Such patients might have nutritional requirements that substantially differ from traditionally suggested requirements. The present system identifies those differences based on the specific patient's health information.

The dose determination is an optimization of maximizing therapeutic effect while minimizing likelihood of adverse effects for the combination of food/nutrients taken. This will consider data relating to pharmacokinetics, distribution, prior toxicity and efficacy determinations, age, metabolism, and any other criteria related to toxicity and efficacy outcomes. In other words, known data is compiled from prior clinical data studies (Phase 1 through Phase 4 trials) and existing EMR/EHR and nutritional databases and compared to specific patient data in order to predict proper safe and efficacious nutritional and dietary recommendations. The method can further include dispensing the food/nutrients to the patient in the prescribed and determined dose 40. In the case of dispensing, the present invention ensures sufficient evaluation criteria was provided before suggesting an outcome. In certain cases various data points might be collected over a period of time as a prerequisite to suggesting an optimized nutrition plan. The present invention further provides for a logic engine (i.e. a computer program) for performing the method, including an algorithm stored on non-transitory computer readable media for collecting patient data 10 and storing the patient data in a database 50, analyzing the patient data in view of outside data 20, and determining a dose for each food/nutrient with output data 30.

"Food" as used herein, can be any raw or unprepared food substance or prepared food. For example, a food can be flour, fruit, vegetables, oils, a sandwich, soup, a pasta dish, etc. Any food component can be analyzed to determine its nutritional value.

"Nutrient" as used herein, can be any component of a food substance that has nutritional value. There are many different nutrients, such as nutrients for bone growth (vitamin D, magnesium, calcium, vitamin A, vitamin K), nutrients for metabolism (vitamin B complex (B1, B2, B3, B5, B6, B12), fats (omega-3, omega-6), nutrients for protein absorption (vitamin E), nutrients for the immune system (vitamin C), and electrolytes (sodium, chloride, zinc, potassium, $HPO_{42}$ Phosphate). Nutrients can be in the form of supplements or be present in food.

"Disease state" as used herein, refers to a patient's current physiological state such as having cancer, diabetes, metabolic syndrome, etc.

Most generally, the algorithm used in the present invention is Data Input→Central AI↔Healthcare Professional. The data input can be from, but is not limited to, clinics, electronic medical records (EMRs), pharmaceutical companies, private databases, CROs, or entered by the patient into a tracking system. The healthcare professional can be, but is not limited to, a nutritionist, MD, pharmacist, hospital, insurer, nurse, laboratory professional, or other medical professional. The healthcare professional can then input data regarding the patient back into the central AI such as, but not limited to, patient data from monitors (including at a medical facility and personal monitors such as smart devices), data from EMRs, insurance information, as well as information gathered from patient during intake or evaluation. Any of the data being collected and received can be in real time. From the data input to the central AI, the AI performs analysis on the complex combination of inputs relating any and all variables that effect food/nutrient metabolism, with dimensions relating how these variables are effected by dosing of additional consumed food/nutrients. Generally, trends are identified to associate an input or combination of inputs with successful or unsuccessful outcomes.

The AI applies patient's specific disease state, physiology, metabolism, etc. for food/nutrients being taken to a previously trained model to determine an optimized food/nutrient plan. As these factors can be induced to change by a change in disease state, drug induced changes, etc., real time monitoring of these changes can assist in real time nutritional dosing adjustments. While such a system may not be practical for all home care but is practical for patients already on monitors and mechanically/digitally receiving drugs and/or food/nutrients. Nutritional and dietary monitoring can take place in the form of meal/nutritional intake logging applications. Information from such intake logging applications can help inform the algorithm.

The AI creates a personalized model relating dosing to patient condition and effect of other food/nutrients on that condition which effect efficacy of the overall suggested nutritional plan. The AI accounts for complex interconnected variables to account for complicated relationships while providing simple output of recommended dosing range of multiple food/nutrients, or actually in real time administer those food/nutrients. The general factors/variables in the matrix can be, but are not limited to, age of patient, weight of patient, disease state, effect of disease state on nutrition, drugs currently being taken along with known side effects of drugs alone and in combinations with other drugs, known toxicity range as related to ED 50 and other dose response points of interest, efficacy ranges, and chronic treatment effect versus acute treatment (one time dosing versus dosing over time). Such factors can be gathered from clinical studies along with other information as necessary and then the patient can be fit into matrix to determine dosing for food/nutrients needed.

Figure 2:
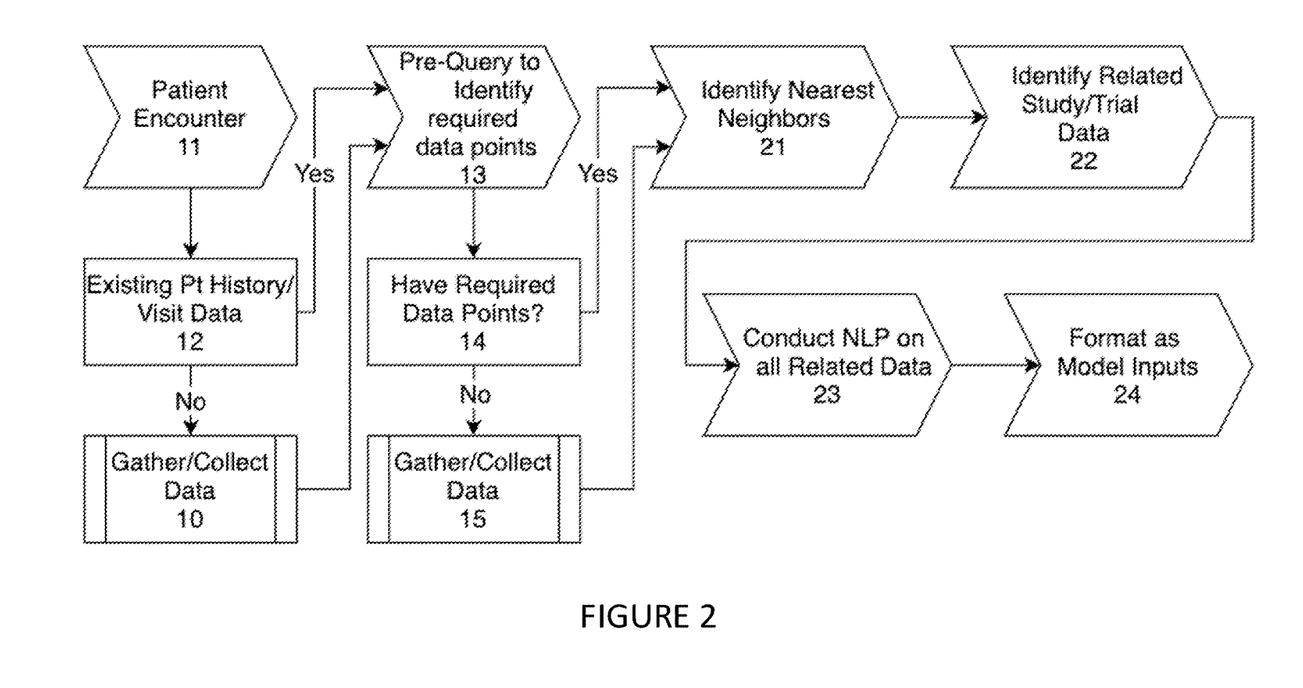
FIG. 2 is a schematic of the method of the present invention.
Figure 4:
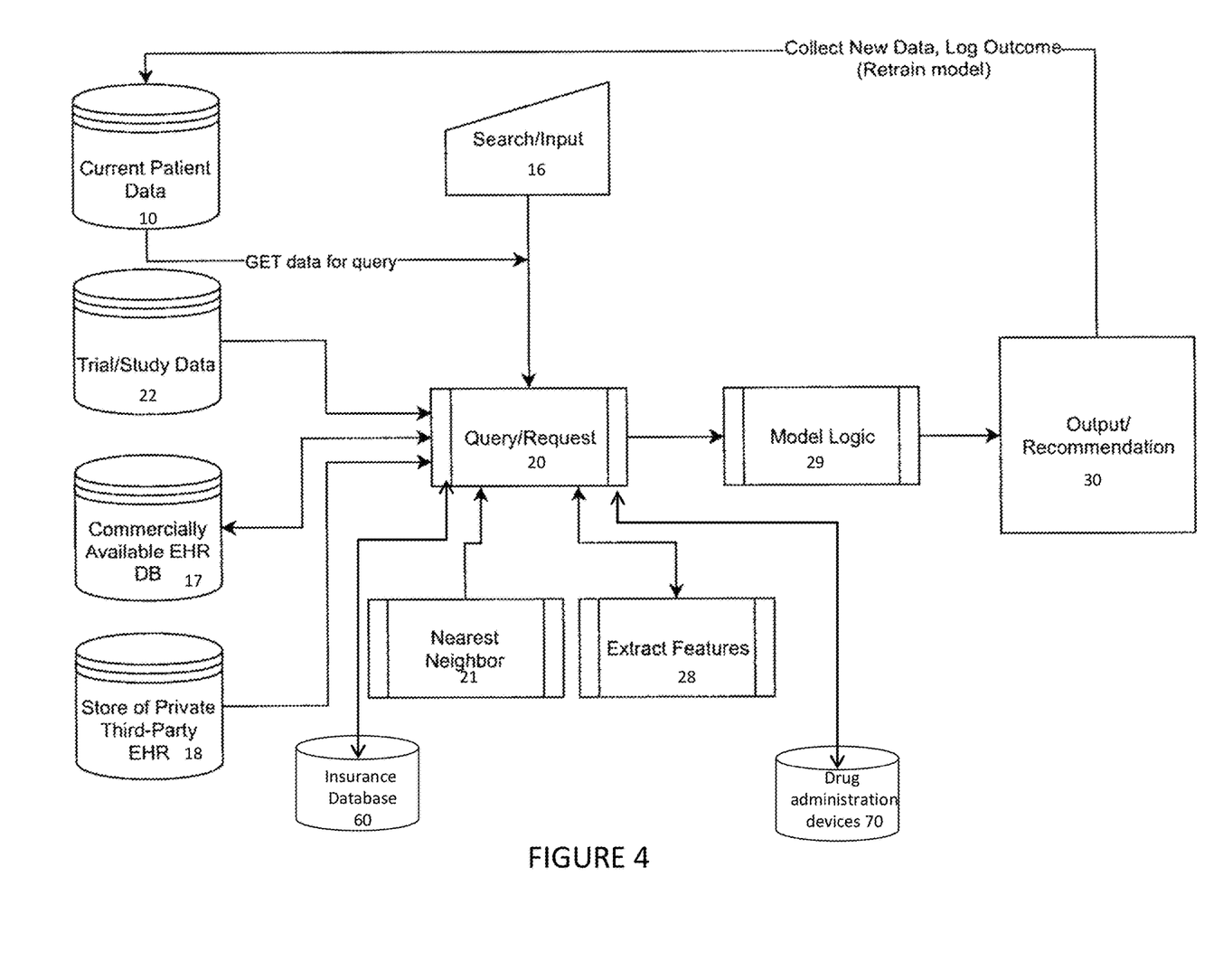
FIG. 4 is a schematic of the method of the present invention.

The method and logic engine are shown in greater detail in FIGS. 2 and 4. At a patient encounter 11, it is first determined if there is any existing fit history or visit data 12. If not, patient data can be collected 10 as detailed below. A pre-query 13 is performed to identify any required data points to perform an analysis. If the required data points 14 are not present, then they are gathered or collected 15. Next, the nearest neighbors are identified 21, related study/trial data is identified 22, Natural Language Processing (NLP) is conducted on related unstructured data 23, before being conditioned as program inputs 24. Natural Language Processing is a type of AI that extracts features from unstructured text, such as, but not limited to, patient notes or items appearing in 'other' categories in drug trials. The unstructured data can also list additional side effects or notes from any informal exams. In the case of nutrition, the unstructured data includes any patient description of their current intake or habits.

Various data is collected about the patient 10 and entered into a database 50 on computer readable media. This includes symptoms, diagnoses, and proposed drugs/treatments 16 that the patient has been prescribed to take by a doctor or other medical professional. More specific data can be collected from analysis of blood and urine samples related infectious disease, metabolism, presence of antigen indicated disease (such as cancer, MS, etc.), patient temperature, blood pressure and other data routinely or additionally collected by the health care professional or present in the patient's electronic health record.

Fixed demographics can be collected, such as, but not limited to, age, gender, race, height, known drug interactions, and body composition (fat, muscle content). All of these criteria, including genetic inclination to food/nutrient metabolism and general metabolism, resistance and susceptibility to disease, and other related criteria are analyzed, as each can be individually pertinent related to the metabolism of each individual food/nutrient prescribed and taken by the patient, as well as the combined effects of each of the food/nutrients on each other. In other words, consideration regarding the food/nutrient individual effects on the patient as well as the effects of the combined combination of food/nutrients (along with effects of drugs) is considered.

Temporal values can be collected, such as, but not limited to, historic values from existing electronic medical records (EMR) or electronic health records (EHR), current/up to date values, cholesterol, blood pressure, weight, and diagnostics related to a specific ongoing disease. The database 50 can be in electrical connection with commercially available EHR databases 17 and private third-party EHR databases 18 to search for relevant data and extract data to the database 50 for analysis. Patient data related to diet (i.e. specific foods eaten often, especially ones known to have interactions with drugs) and nutritional supplements can also be collected, as well as exercise habits.

Genetic components can be collected, such as, but not limited to, key genetic markers, whole genome data from genetic testing/ancestry sites, or test results from any type of genetic tests. Genetic components are important not just for markers for known food/nutrient efficacy, but also for generating ethnicity and demographics features for multidimensional nearest neighbor calculations (further described below).

Various imaging can be collected, such as, but not limited to, CAT scans, CT scans, X-rays, MRI, ultrasounds, PET scans, or other visual analyses. Reports from imaging studies are analyzed and encoded using an NLP algorithm to extract features. These features, along with structured findings from a radiologist are used to inform the model.

Unstructured data can also be collected, such as, but not limited to, any patient notes over time. Natural language can be processed into a network of classifiers to identify propensities for certain risk factors, given certain patient notes. For example, there may be a correlation between the presence of hygiene concerns in a patient note and reduced likelihood of adherence to a food/nutrient therapy regime. Unstructured patient data includes notes by healthcare professionals as well as information collected directly from the patient including responses questionnaires, intake forms, etc.

This patient data structure, when fully populated, contains the full digital footprint needed to make queries into the logic engine. Instead of a fixed patient data structure, the patient model is fluid, and its makeup of fields is determined by the desired outcome of the model. This reflects the fluidity of the patient's stasis as the patient's condition ultimately requiring the need for food/nutrient consumption and the related dosing is fluid as the patient initially succumbs to a disease, is treated with drugs, and then hopefully recovers from the disease. As the patient's stasis changes and hopefully returns to homeostasis, dosing can be altered.

The logic engine can request supplemental data 13 based on the patient data. Once trained, the logic engine has the ability to apply a discrete weighting regime to extracted features 28 based on their significance, i.e. request a blood level or demographic data point prior to making a dosing recommendation, imaging, pharmacogenomics testing, lifestyle questions, or any other type of diagnostics required. Different food/nutrient combinations will require different sets of supplemental data. Additional data selection can be weighted by importance, invasiveness, cost, and availability. For example, if a certain test is not available or prohibitively invasive, the logic engine reacts accordingly by being transparent with the decreased accuracy or exposure to potential risk.

Since the required input data varies on numerous conditions, essential data points are unknown until the basic query has started. If no further data is needed, the logic of the present invention can continue without additional input. Also, data can be weighted, and combinations of data can be weighted.

Figure 5:
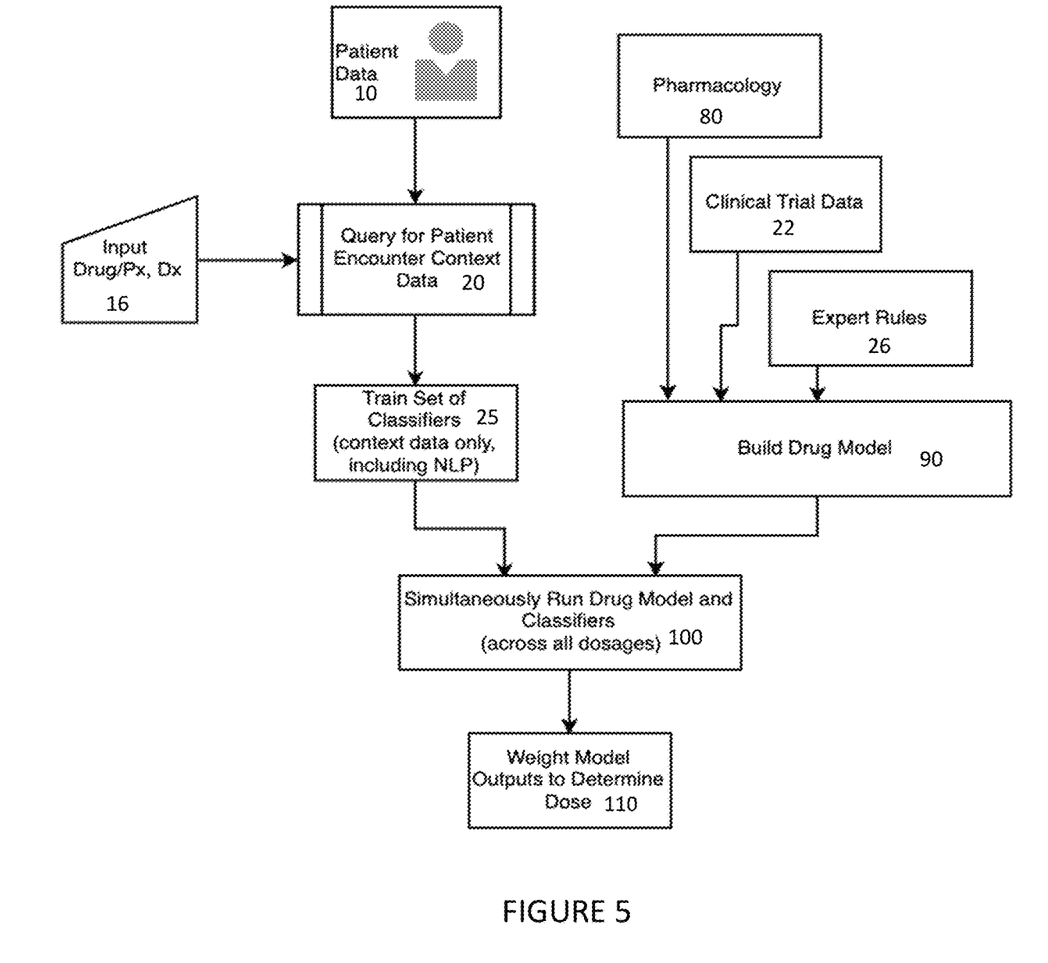
FIG. 5 is a schematic of the method of the present invention.

The database 50 can also collect information relating to any drugs desired to be prescribed (i.e. pharmacology information 80, shown in FIG. 5). Pharmacology information 80 can include drug mechanism of action, the safe dosage range, the suggested dosing strategy, and other pharmacological properties such as liberation, absorption, distribution, metabolism, and excretion. These factors and any other available information are taken into consideration to develop the model.

Pharmacology information 80 can include information from animal studies that can be used for initial dosing in humans. This can particularly be useful in designing FDA drug trials and especially for INDs. For example, allometric scaling can be performed wherein the dose in an animal is normalized based on body surface area to humans (FDA Guidance for Industry, Estimating the Maximum Safe Starting Dose in Initial Clinical Trials for Therapeutics in Adult Healthy Volunteers; Nair, et al. Journal of Basic and Clinical Pharmacy, 2016). Allometric scaling can be useful in drugs having lesser hepatic metabolism, low volume of distribution, and are excreted by renal route. Scaling based on weight can also be used. Other methods may need to be used for the following drugs according to the FDA. 1. Therapeutics administered by alternative routes (e.g., topical, intranasal, subcutaneous, intramuscular) for which the dose is limited by local toxicities. Such therapeutics should be normalized to concentration (e.g., mg/area of application) or amount of drug (mg) at the application site. 2. Therapeutics administered into anatomical compartments that have little subsequent distribution outside of the compartment. Examples are intrathecal, intravesical, intraocular, or intrapleural administration. Such therapeutics should be normalized between species according to the compartmental volumes and concentrations of the therapeutic. 3. Proteins administered intravascularly with Mr>100,000 daltons. Such therapeutics should be normalized to mg/kg.

Human equivalent dose (HED) from an animal dose can be determined if the animal no observed adverse effect level (NOAEL) is known. The NOAEL is the highest dose level that does not produce a significant increase in adverse effects in comparison to the control group. The equation below uses a correction factor for body surface area:

$$\text{HED (mg/kg)} = \text{Animal NOAEL (mg/kg)} \times (\text{weight}_{animal} \text{[kg]}/\text{weight}_{human} \text{[kg]})^{(1-0.67)}$$

Table 1 shows conversion factors for interspecies dose conversions for NOAELs.

Prescriptions of certain drugs (or combinations of drugs) can require pharmacogenomic testing to check for certain markers. These markers can help decide between different classes of drug, circumvent known risk factors, as well as optimize the dosages. Since the effectiveness of a therapy is influence by the presence of certain markers, the results from genetic testing can be critical inputs. Pharmacogenomic testing is widely used when evaluating medications used in the treatment of ADD/ADHD and depression, anticoagulants, and others. The use and availability of data from pharmacogenomic testing is on the rise due to decreasing costs.

Mimicking the human expert decision making process, all data pertinent to making an informed decision must be made available and formatted prior to running the logic engine. The logic engine can proceed with missing data points, however, accuracy and therefore confidence in the decision are reduced.

Nearest neighbor data can be identified 21. A key aspect to the success of the present invention is the use of data from similar patient data markers. A "nearest neighbor", as used herein, can be persons that have similar patient data and/or underwent a treatment plan with similar food/nutrient combinations. Identifying existing records similar to the patient in treatment is a key component to the accuracy of the logic engine. A multi-dimensional nearest neighbor algorithm is used to find those individuals from existing sets, i.e. a

TABLE 1

Conversion of Animal Doses to Human Equivalent Doses Based on Body Surface Area

| Species | To Convert Animal Dose in mg/kg to Dose in mg/m2, Multiply by km | To Convert Animal Dose in mg/kg to HEDa in mg/kg, Either: | |
| --- | --- | --- | --- |
| | | Divide Animal Dose By | Multiply Animal Dose By |
| Human[a] | 37 | — | — |
| Child (20 kg)[b] | 25 | — | — |
| Mouse | 3 | 12.3 | 0.08 |
| Hamster | 5 | 7.4 | 0.13 |
| Rat[a] | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 | aAssumes 60 kg human. For species not listed or for weights outside the standard ranges, HED can be calculated from the following formula: HED = animal dose in mg/kg × (animal weight in kg/human weight in kg)0.33
bThis km value is provided for reference only since healthy children will rarely be volunteers for phase 1 trials
cFor example, cynomolgus, rhesus, and stumptail A safety factor can also be applied to the HED to provide a margin of safety for humans. Generally, a safety factor of 10 is used, but this can be adjusted based on different circumstances (raised when there is reason for increased concern, lowered when concern is reduced because of available data that provide added assurance of safety).

Parenteral administration doses can be calculated from the following equation. The results can be checked against FDA maximum injection volume guidelines.

$$\text{Injection volume (mL)} = \text{animal weight (kg)} \times \text{animal dose (mg/kg)}/\text{concentration (mg/mL)}$$

K-Nearest Neighbor (KNN) algorithm. The KNN algorithm is a clustering algorithm and acts as a non-parametric untrained classifier that evaluates the overall similarity between two patients/subjects based on the degree of differences across multiple features. The flexibility of such an algorithm allows consideration of many parameters when searching for pertinent context data. Weights on certain factors can vary depending on the type of diagnosis and food/nutrient. For example, a patient might be more willing to risk side effects in exchange for efficacy. These similar patient profiles are grouped into subsets to look for trends that can be used to optimize the treatment plan of the given patient. While the KNN algorithm can be preferred, other clustering algorithms can also be used, such as, but not limited to, K-Means, Affinity Propagation, Mean Shift, Spectral Clustering, Support Vector Machines. One advantage of KNN over other techniques is that it is easily scalable across many dimensions. Further, from case-to-case differing dimensions and weights are easily included.

The purpose of the KNN algorithm is to find patients most similar to the present patient. Once identified, the "neighboring" patient data, including treatment plan and outcome, are used to evaluate the present subject. To make the identification, we evaluate the differences in each parameter comprising the patient data structure. While most commonly used with continuous values (weight, age, LDL level, etc.), the algorithm can be used with discrete values as well (race/ethnicity, familial history, presence of certain symptoms, etc.). The differences across each parameter are combined using a weighting scheme such that a normalized 'distance' is produced representing an overall difference metric between two patients. The distance calculation between two patients is achieved using a regression-type KNN algorithm. Key to the regression evaluations is the Mahalanobis distance. The Mahalanobis distance evaluates to a Euclidian distance since the covariance matrix is always the identity matrix, i.e., one parameter in this case is never to be compared independently with another parameter. The benefit of adapting the Mahalanobis distance instead of using pure Euclidian distance is that Mahalanobis distance includes the measurement of the number of deviations away from the norm. While the actual standard deviation is not always ideal, an equivalent term is used.

If the present patient $P_1$ has a set of parameters where $P_1 = \{\mu_{1P1}, \mu_{2P1}, \mu_{3P1}, \ldots \mu_{NP1}\}$ and an arbitrary patient, $P_\beta$, where $P_\beta = \{\mu_{1P\beta}, \mu_{2P\beta}, \mu_{3P\beta}, \ldots \mu_{NP\beta}\}$, then the distance, D, between the two patients is:

$$D_1(P_1, P_\beta) = \sqrt{\sum_{i=1}^{N}(\mu_{iP1} - \mu_{iP\beta})^2}$$

Several adaptations are needed to the above generalized equation. Mainly, handling a weighting schema. Most simply, a set of weights, W, should be created with each parameter in P being assigned a weight. Weights can be applied using any technique. Shown below is an intuitive 1-10 linear weighting schema. If $W = \{\rho_1, \rho_2, \rho_3, \ldots \rho_N\}$, then the distance, D, can be evaluated by:

$$D_2(P_1, P_\beta) = \sqrt{\sum_{i=1}^{N}\rho_i(\mu_{iP1} - \mu_{iP\beta})^2}$$

In the above examples for $D_1$ and $D_2$ continuous values are used for $\mu_N$. In this application, continuous values can be integers or rational numbers. Discrete values must be handled in a special manner. Since there is no intuitive value for the difference between two ethnicities, one must be manually supplied in a lookup table. Algorithmically, parameters with continuous values should be summated using the squared difference while parameters with continuous values are summated manually. The same $W = \{\rho_1, \rho_2, \rho_3, \ldots \rho_N\}$ weighting schema applies to discrete parameters as well.

The threshold for evaluating whether or not another patient is sufficiently similar to the present patient is situational. The ideal number of similar subjects is to be optimized on a case-to-case basis when there exists sufficient training data.

KNN algorithms have been used before. For example, U.S. Pat. No. 10,123,748 (IBM) discloses a Patient Risk Analysis method that uses KNN to find similar patients. U.S. Pat. No. 7,730,063 discloses a personalized medicine method that also mentions KNN as a potential algorithm for finding similar patients. The present invention's ability to include continuous and discrete parameters as well as customized weights in the KNN differentiates over these prior art methods.

The inputs to the logic engine are broad and complex. AI techniques such as the KNN algorithm are applied to the inputs to precondition the data. By taking this step to precondition data, the following processing steps are simplified.

The logic engine employs a combination of artificial intelligence techniques, both supervised and unsupervised. Instead of using a broad-scale program that is trained once, the logic engine in the present invention is unique to the inputs and is therefore trained on demand. The benefit to this technique is to emphasize the individuality of the patient and the symptoms.

Figure 3:
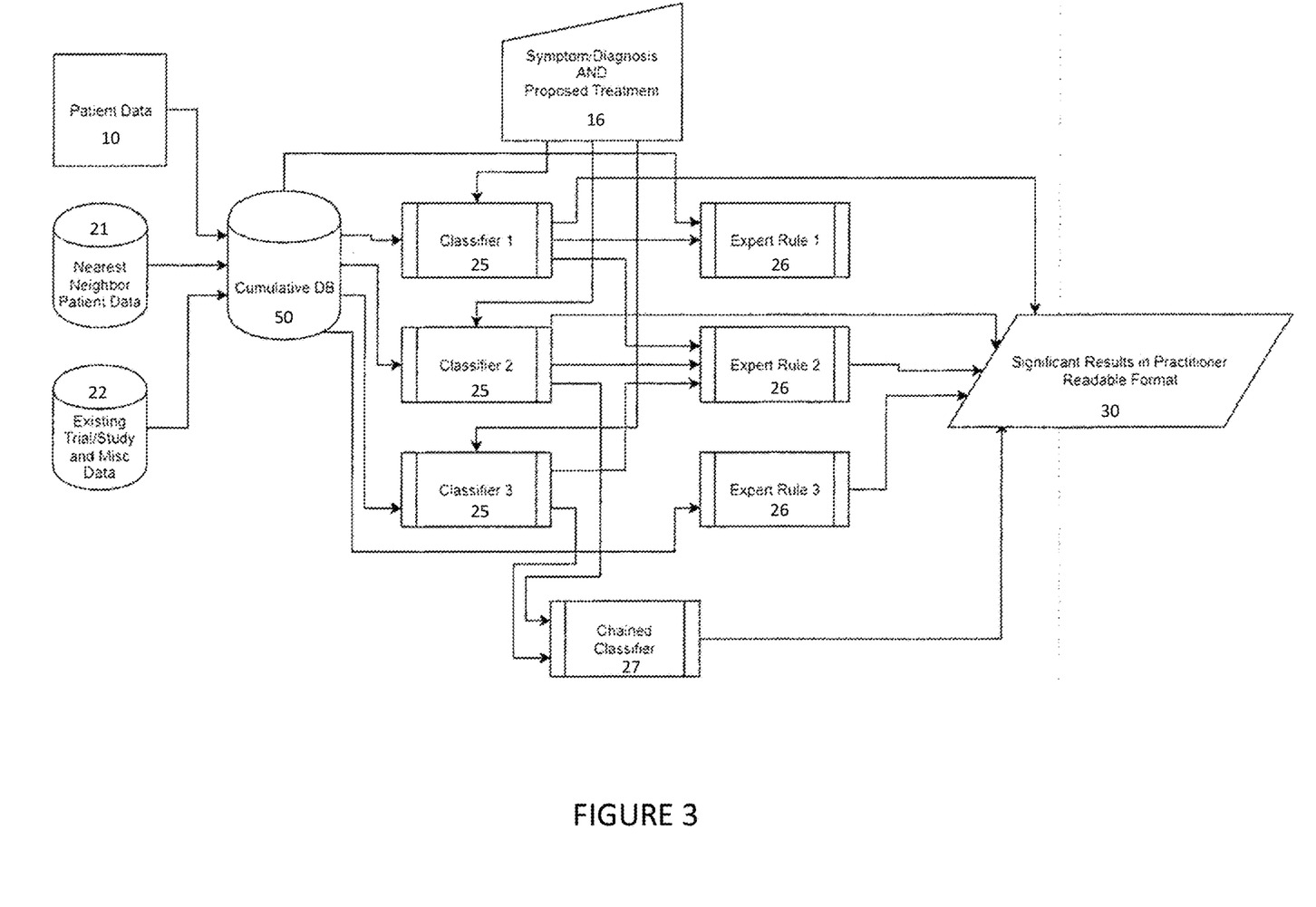
FIG. 3 is a schematic of classifiers and expert rules in the method.

Most broadly, and as shown in FIG. 3, the present invention includes model logic 29 composed of a series of classifiers 25, some of which offer direct outputs (such as the likelihood for an occurrence of an interaction or the presence of a certain side effect), while others perform intermediary steps. Classifiers 25 and expert rules 26 implemented in series is a strategy known as chaining 27, a process that takes advantage of the smaller preprocessing steps conducted by earlier-staged processing. Processing data using classifiers 25 in this way codes the patient information into a format suitable for use in existing artificial intelligence techniques. Most commonly, this involves assigning a quantitative element to inherently non-quantitative data. Data points, such as the presence of a side effect, are turned into features. Data elements can be Boolean or continuous depending on the type. Each individual data element is assigned a confidence and a weight. The confidence is a representation of the accuracy of the element, while the weight represents the importance.

The expert system also contains a series of rules 26 prepopulated by practitioners. These rules 26 can be drug or drug-class specific and compose the supervised learning aspect of the AI. In the spirit of fuzzy logic systems, each rule 26 is assigned a varying degree of truth, establishing a crude weighting scheme.

The classifiers 25 and the model 90 are ran simultaneously across all possible dosage ranges 100. For each dosage, classifications with confidence intervals are calculated. The generic model is run using the same set of dosages mapped out to the same classifiers used when evaluating context data. The outputs from both models are weighted and combined to determine the optimal dose 110 in the output 30.

A major differentiator with the present invention relates to the mimicked expert output 30 of the logic engine. The output of the logic engine is an overall comprehensive analysis of the present patient, the diagnosis, and the primary method of treatment with dosages for each diagnosis. Any notable findings related to food/nutrient interaction (either with other food/nutrients or with drugs taken by the patient), decreased efficacy, or side effect management are incorporated into the output. It accomplishes producing an output based on data not accessible by the practitioner or nutritionist. Analysis is provided to determine output presently not considered by the practitioner. Presently, the only assistance to the practitioner or nutritionist is in the nature of do or do not do. That is, do give certain drugs together or do not based on general know toxicities. Nothing is available that assists in not only minimizing toxicity, but also maximizing efficacy of food/nutrient intake along with drug combinations in view of a patient's disease state.

The format of the output 30 can be a practitioner readable report with information being displayed in a manner to easily allow the user to identify categories of alerts. Certain outputs 30 can alter the course of a treatment altogether while other times an output might reinforce a direction in an attempt to mitigate an already known side effect. When applicable, the likelihood or confidence approximation is presented as well. This transparent output 30 format is all in an attempt to synthesize relative information when the practitioner is facing a treatment decision.

The output 30 can also be sent to a pharmacy or self-dispensing machine where the determined dose of each food/nutrient can be prepared for the patient 40. The output 30 can also provide the patient with instructions of how to take each food/nutrient and side effects to watch out for, as well as contraindications with commonly taken over the counter medications, supplements, and food. The output 30 can be sent wirelessly to any medical professional or the patient to read on a mobile device, tablet, laptop, or desktop computer. While nutritionists can use the logic engine to initially prescribe food/nutrients at a certain dose to a patient, the logic engine can also be used by pharmacists to check a prescription in view of the other drugs that the patient is currently taking to make sure that the dose is correct and to reduce side effects. The output 30 can also be sent to a device that can create a personalized supplement/food item that includes the necessary nutrition that the patient requires. For example, a pill can be compounded with various vitamins and minerals, or a meal or drink can be produced or created that includes required nutrients from various raw material ingredients.

The database 50 can also be in electronic communication with food/nutrient and/or drug administration devices 70. This can be to the extent of real time dosing, administration, patient data gathering, and dosing adjustment based on the real time data. In other words, after running the logic engine, and based on the recommended doses of food/nutrients taken by the patient, the drug administration device 70 can receive updated dose information and adjust future doses accordingly. Electronic communication can be wireless or wired (such as with BLUETOOTH® or downloadable with a USB connection) and signals can be sent at the time that a dose is administered. These devices can include, but are not limited to, transdermal patches, intravenous drips, self-injection and auto-injection devices, wearable injection devices, and implantable drug delivery devices.

The present invention has several advantages over the prior art. The present invention checks nearest neighbor patient outcomes when given similar food/nutrient combinations. Even if there is no indicated complication, a decrease in efficacy or increase in side effects are considered.

Further, outputs of the exam are never limited to an amount of active ingredient, instead, full treatment plans are suggested. This information can be relayed to the patient or used internally for the decision making process. Therefore, the present invention provides a technical effect of providing a treatment plan with dosing of particular food/nutrients to the patient, as well as providing to the patient the recommended doses. There is potential to maximize a treatment plan while acting in accordance with the suggested use of the food/nutrient. Varying treatment plans can be justified if trends suggest preferred outcomes for similar patient profiles. Instead of the present invention being treated as a dosage calculator, it is more so a decision making tool that puts forth all necessary information to the practitioner to make a more informed treatment plans.

The present invention provides advantages to patients because instead of being prescribed food/nutrient combinations at sub-optimal and sometimes sub-efficacious levels, the present invention can initially dose food/nutrients to a patient at nontoxic and efficacious doses.

The present invention provides advantages to nutritionists and healthcare professionals because they no longer have to guess at dosing. The platform also considers the patient's clinical and physical conditions thereby personalizing the patient's prescription.

The present invention can be useful in dosing food/nutrients with any combination of drugs. The drugs can be generally from the classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins. Some specific combinations of drugs that are most commonly used by people include, but are not limited to, lisinopril and atorvastatin, lisinopril and metformin, amlodipine and lisinopril, alprazolam and amphetamine salt combo, amphetamine salt combo and amphetamine salt combo xr, hydrocodone/acetaminophen and alprazolam, amlodipine and atorvastatin, lisinopril and hydrochlorothiazide, atorvastatin and clopidogrel, atorvastatin and metformin, metformin/lisinopril/atorvastatin, clopidogrel/atorvastatin/lisinopril, glipizide/metformin/lisinopril, atorvastatin/amlodipine/lisinopril, amlodipine/hydrochlorothiazide/lisinopril, carvedilol/atorvastatin/lisinopril, atorvastatin/metoprolol/lisinopril, clopidogrel/metoprolol/atorvastatin, lisinopril/carvedilol/furosemide, and amlodipine/metformin/lisinopril.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of dosing food and nutrients for an individual patient, consisting essentially of the steps of:
  collecting data from the individual patient being dosed including electronic medical records, past and current nutritional intake habits, laboratory results, and food and nutrients to be taken by the patient to improve the patient's condition and inputting the data into a database with a central artificial intelligence (AI) stored on computer readable media, wherein the patient has cancer;

the central AI analyzing the individual patient's collected data from the database in view of dosing criteria established based on outside clinical trial data,
wherein the AI extracts from the outside clinical trial data all features relating variables that effect food and nutrient metabolism in a patient and creates a model relating dosing to patient condition and effect of food and nutrients on the condition that effect efficacy of all food and nutrients taken by the patient, wherein the variables include age of patient, weight of patient, disease state, effect of disease state on nutrition, drugs currently being taken along with known side effects of drugs alone and in combinations with other drugs, known toxicity range as related to ED 50, efficacy ranges, and chronic treatment effect versus acute treatment, the AI conducting natural language processing on unstructured data and extracting features from unstructured text of patient notes, notes from informal exams, and patient descriptions of current intake and habits, wherein the AI identifies nearest neighbors of patients from the clinical trial data having similar patient data and/or underwent a treatment plan with similar food and nutrient combinations to the individual patient and identifies related study and trial data with a K-Nearest Neighbor algorithm that calculates a distance between the patient and a neighbor patient using both continuous data and discrete data that is assigned a value and manually supplied to the database, wherein the AI compares the individual patient data to neighboring clinical trial patient data with weighting schemes;
the central AI determining a dose for each food and nutrient taken by the individual patient and maximizing therapeutic effect of each food and nutrient for the individual patient while minimizing adverse effects for the combination of food and nutrients taken for the individual patient, wherein the nutrients include each of vitamin D, magnesium, calcium, vitamin A, vitamin K, vitamin B1, vitamin B2, vitamin B3, vitamin B5, vitamin B6, vitamin B12, omega-3, omega-6, vitamin E, vitamin C, sodium, chloride, zinc, potassium, and $HPO_{42}$ Phosphate, and displaying the dose in a readable report for a practitioner; and
the AI monitoring changes in the patient in real time due to changes in a disease state or drug induced changes, and the AI adjusting the dose for each food and nutrient in real time.

2. The method of claim 1, wherein the individual patient data and outside data is chosen from the group consisting of pharmacokinetics, distribution, prior toxicity and efficacy determinations, age, metabolism, and combinations thereof.

3. The method of claim 1, wherein said collecting step is further defined as collecting fixed demographics, temporal values, genetic components, imaging, and unstructured data.

4. The method of claim 1, wherein said analyzing step includes analyzing a dose of a food or nutrient in combination with a drug chosen from a class consisting of classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins.

5. The method of claim 1, further including the step of dispensing the food and nutrients to the patient in the determined dose.

6. A logic engine for dosing food and nutrients, consisting essentially of an algorithm stored on non-transitory computer readable media for collecting outside clinical trial data to establish criteria for dosing food and nutrients to an individual patient having cancer and storing the outside clinical trial data and individual patient data in a database, analyzing the individual patient's collected data from the database in view of criteria established from the outside clinical trial data with artificial intelligence (AI), wherein the AI extracts from the outside clinical trial data all features relating variables that effect food and nutrient metabolism in a patient and creates a model relating dosing to patient condition and effect of food and nutrients on the condition that effect efficacy of all food and nutrients taken by the patient, wherein the variables include age of patient, weight of patient, disease state, effect of disease state on nutrition, drugs currently being taken along with known side effects of drugs alone and in combinations with other drugs, known toxicity range as related to ED 50, efficacy ranges, and chronic treatment effect versus acute treatment, wherein the AI conducts natural language processing on unstructured data and extracting features from unstructured text of patient notes, notes from informal exams, and patient descriptions of current intake and habits, wherein the AI identifies nearest neighbors of persons having similar patient data and/or underwent a treatment plan with similar food and nutrient combinations to the individual patient and identifies related study and trial data with a K-Nearest Neighbor algorithm that calculates a distance between the patient and a neighbor patient using both continuous data and discrete data that is assigned a value and manually supplied to the database, wherein the AI compares the individual patient data to neighboring clinical trial patient data with weighting schemes, and determining a dose for each food and nutrient to be taken by the individual patient, wherein the nutrients include each of vitamin D, magnesium, calcium, vitamin A, vitamin K, vitamin B1, vitamin B2, vitamin B3, vitamin B5, vitamin B6, vitamin B12, omega-3, omega-6, vitamin E, vitamin C, sodium, chloride, zinc, potassium, and $HPO_{42}$ Phosphate, wherein the algorithm provides an output in the form of a practitioner readable report, and wherein the AI monitors changes in the patient in real time due to changes in a disease state or drug induced changes, and the AI adjusts the dose for each food and nutrient in real time.

7. The logic engine of claim 6, wherein said algorithm is defined as data input→central AI↔healthcare professional.

8. The logic engine of claim 7, wherein said data input is chosen from the group consisting of clinics, electronic medical records (EMRs), pharmaceutical companies, private databases, and CROs, and wherein said healthcare professional is chosen from the group consisting of nutritionist, MD, pharmacist, hospital, insurer, nurse, and laboratory professional, and wherein said healthcare professional inputs data including patient data from monitors, data from EMRs, insurance information, and information gathered from the patient during intake or evaluation.

9. The logic engine of claim 6, wherein said logic engine can request supplemental data based on the individual patient data and weight data by importance, invasiveness, cost, and availability.

10. The logic engine of claim 6, wherein said logic engine includes model logic having a series of classifiers and expert rules implemented in series, and said classifiers and a model are run simultaneously across all possible dosage ranges, and outputs are weighted and combined to determine an optimal dose.

11. The logic engine of claim 6, wherein the practitioner readable report is sent to a place chosen from the group consisting of a pharmacy, a self-dispensing machine, a medical professional, and the individual patient.

12. The logic engine of claim 11, wherein said output includes instructions of how to take each food and nutrient, side effects to watch out for, and contraindications with commonly taken over the counter medications, supplements, and food.

13. The logic engine of claim 11, wherein said output is sent to a device that creates a personalized supplement or food item including the necessary nutrition that the patient requires.

14. The logic engine of claim 6, wherein said logic engine is in electronic communication with drug administration devices chosen from the group consisting of transdermal patches, intravenous drips, self-injection and auto-injection devices, wearable injection devices, and implantable drug delivery devices.

\* \* \* \* \*